Figure 1:
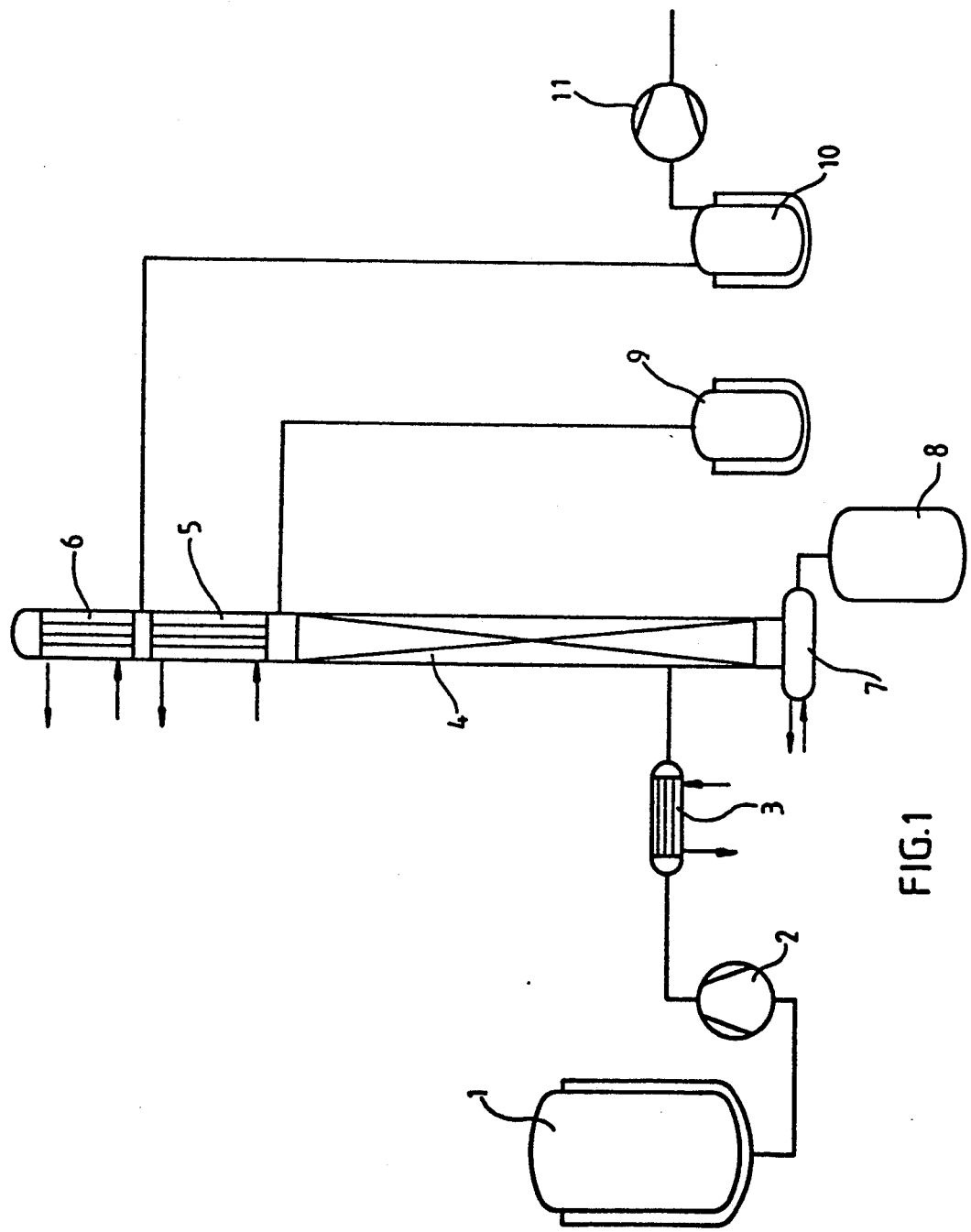

United States Patent [19]

Hauner et al.

[11] Patent Number: 5,284,969
[45] Date of Patent: Feb. 8, 1994

[54] PROCESS FOR THE PRODUCTION OF POLYISOCYANATES

[75] Inventors: Andreas Hauner, Cologne; Hans-Joachim Hennig, Leverkusen, both of Fed. Rep. of Germany

[73] Assignee: Bayer Aktiengesellschaft, Leverkusen, Fed. Rep. of Germany

[21] Appl. No.: 972,675

[22] Filed: Nov. 6, 1992

[30] Foreign Application Priority Data

Nov. 14, 1991 [DE] Fed. Rep. of Germany ....... 4137428

[51] Int. Cl.$^5$ .......................................... C07C 263/04
[52] U.S. Cl. ................................ 560/345; 203/28; 203/60; 203/69; 560/352
[58] Field of Search ............... 560/345, 352; 203/28, 203/60, 69

[56] References Cited

U.S. PATENT DOCUMENTS

| | | | |
|---|---|---|---|
| 2,409,712 | 10/1946 | Schweitzer | 560/345 |
| 3,870,739 | 3/1975 | DeLaMater et al. | 560/345 |
| 3,919,278 | 11/1975 | Rosenthal et al. | 560/345 |
| 3,919,279 | 11/1975 | Rosenthal et al. | 560/345 |
| 3,919,280 | 11/1975 | Rosenthal et al. | 560/345 |
| 3,962,302 | 6/1976 | Rosenthal et al. | 560/345 |
| 3,992,430 | 11/1976 | Bacskai | 560/345 |
| 4,003,938 | 1/1977 | Koenig et al. | 560/345 |
| 4,081,472 | 3/1978 | Tsumura et al. | 560/345 |
| 4,195,031 | 3/1980 | Reichmann et al. | 560/345 |
| 4,195,032 | 3/1980 | Koster et al. | 560/345 |
| 4,330,479 | 5/1982 | Merger et al. | 560/345 |
| 4,530,796 | 7/1985 | Mattner et al. | 560/345 |

FOREIGN PATENT DOCUMENTS 323514 7/1989 European Pat. Off. .

Primary Examiner—Jose' G. Dees
Assistant Examiner—Vera C. Clarke
Attorney, Agent, or Firm—Joseph C. Gil; N. Denise Brown

[57] ABSTRACT

A process for the continuous catalyst-free production of polyisocyanates by thermal decomposition of the N-substituted carbamic acid esters corresponding to the polyisocyanates, in which the carbamic acid esters to be decomposed, in the form of a 5 to 90% by weight solution in an inert high-boiling solvent, are heated to a temperature of 100° to 400° C. and are subsequently introduced with expansion as a sidestream into a distillation column (4), in the sump of which a pressure of 0.001 to 5 bar and a temperature of 150° to 400° C. are maintained so that the high boiler is kept boiling in the sump, and the decomposition products are simultaneously condensed continuously and selectively at the head of the distillation column. The high boiler, which optionally contains impurities, is continuously removed via the sump outlet in a quantity substantially corresponding to the quantity of high boiler introduced into the column as solvent for the carbamic acid ester.

6 Claims, 1 Drawing Sheet

PROCESS FOR THE PRODUCTION OF POLYISOCYANATES

BACKGROUND OF THE INVENTION

This invention relates to a new process for the continuous production of organic polyisocyanates, more particularly diisocyanates, by thermal decomposition of the carbamic acid esters on which they are based.

It has been known for many years that N-substituted urethanes can be split into isocyanates and alcohol [H. Schiff, Ber. Dtsch. Chem. Ges. 3, 649 (1870); A. W. Hoffmann, Ber. Dtsch. Chem. Ges. 3, 653 (1870)].

Some time ago, it was found that the decomposition reaction can be carried out with various advantages in the presence of high-boiling solvents for the carbamic acid esters. Thus, U.S. Pat. No. 3,919,278, for example, describes a process for the production of aromatic polyisocyanates in a decomposition reactor surmounted by a distillation column using auxiliary solvents of the type in question and also a carrier gas to improve the removal of the decomposition products formed during the decomposition reaction from the reaction mixture. U.S. Pat. No. 3,962,302 describes a similar process. Both processes result in relatively poor yields which is presumably attributable to the fact that the polyisocyanates formed as decomposition products are difficult to separate from the decomposition medium. It is presumably for this reason that, according to DE-OS 2 530 001, the decomposition medium is subjected to separate working up to recover the diisocyanate present therein.

In addition to these processes carried out in the absence of catalysts, there are also processes in which the yield is supposed to be increased by the use of various catalysts. Relevant publications are, for example, U.S. Pat. No. 3,919,279, DE-OS 2,635,490, DE-OS 2,942,543 or EP-A-0,323,514. It is obvious that the use of catalysts involves certain disadvantages compared with a catalyst-free process. For example, traces of catalyst can never be completely prevented from entering the end products and undesirably affecting their properties. In addition, the working up of the auxiliary solvent is complicated by the presence of the catalysts.

Accordingly, the problem addressed by the present invention was to provide a new process for the production of organic polyisocyanates, more particularly diisocyanates, by decomposition of the corresponding carbamic acid esters which would readily enable the diisocyanates to be continuously produced in high yields in the absence of catalysts.

This problem has been solved by the provision of the process according to the invention which is described in detail hereinafter.

DESCRIPTION OF THE INVENTION

The present invention relates to a process for the continuous catalyst-free production of polyisocyanates by thermal decomposition of the N-substituted carbamic acid esters which correspond to the polyisocyanates at 150° to 400° C. in a sump-heated distillation column serving as a decomposition reactor, with subsequent separation of the decomposition products into two fractions. Fraction I consists predominantly of the isocyanate component and fraction II consists predominantly of the alcohol component of the carbamic acid ester. The decomposition reaction is carried out in the presence of a high boiler which is a solvent for the carbamic acid esters, is inert to the carbamic acid esters and the decomposition products, boils under the pressure and temperature conditions prevailing in the sump of the distillation column, and has a boiling point under those pressure conditions which is at least 10° C. above the boiling point of the polyisocyanate formed. The process is characterized in that the carbamic acid esters to be decomposed, which are in the form of a 5 to 90% by weight solution, are heated above the decomposition pressure to a temperature of 100° to 400° C., but above the melting point of the polyurethane, and are subsequently introduced with expansion as a sidestream into the distillation column (4), in the sump of which a pressure (decomposition pressure) of 0.001 to 5 bar and a temperature of 150° to 400° C. are maintained so that the high boiler is kept boiling in the sump. The decomposition products are simultaneously condensed continuously and selectively at the head of the distillation column in the form of fractions I and II, while the high boiler which optionally contains impurities is continuously removed via the sump outlet in a quantity which substantially corresponds to the quantity of high boiler introduced into the column as solvent for the carbamic acid ester.

The process may be carried out, for example, in the apparatus illustrated in the drawing (FIG. 1). In the drawing, (1) is a heatable storage tank for the carbamic acid ester solution to be decomposed;
(2) is a heatable metering pump for this solution;
(3) is a heat exchanger for preheating the solution of the carbamic acid ester to be decomposed;
(4) is the distillation column serving as decomposition reactor;
(5) is a dephlegmator;
(6) is a condenser;
(7) is the sump heating system, for example in the form of a circulation heater;
(8) is the sump drainage tank;
(9) is the storage tank for the polyisocyanate fraction I;
(10) is the storage tank for the alcohol fraction II provided with a cooling system and
(11) is a vacuum pump.

The carbamic acid esters to be used in the process according to the invention are compounds corresponding to the general formula $R^1(NHCOOR^2)_n$, in which $R^1$ is an aliphatic hydrocarbon radical containing a total of from about 4 to 12 carbon atoms and, optionally, bearing inert substituents; a cycloaliphatic hydrocarbon radical containing a total of from about 6 to 15 carbon atoms and, optionally, bearing inert substituents; an araliphatic hydrocarbon radical containing a total of from about 7 to 10 carbon atoms and, optionally, bearing inert substituents; or an aromatic hydrocarbon radical containing a total of from about 6 to 15 carbon atoms and, optionally, inert substituents;

$R^2$ is an aliphatic hydrocarbon radical containing from about 1 to 20 carbon atoms, a cycloaliphatic hydrocarbon radical containing from about 5 to 15 carbon atoms or an aromatic hydrocarbon radical containing from about 6 to 15 carbon atoms and n is an integer of from 2 to 5.

The carbamic acid esters preferably used in the process according to the invention are those corresponding to the above formula in which $R^1$ is an aliphatic hydrocarbon radical containing a total of from 4 to 12 and, more particularly, from 5 to 10 carbon atoms; a cycloaliphatic hydrocarbon radical containing from 6 to 15 carbon atoms; a xylylene radical or an aromatic hydrocarbon radical containing a total of from 6 to 15 carbon atoms and, optionally, bearing methyl substituents and/or methylene bridges;

$R^2$ is an aliphatic hydrocarbon radical containing from 1 to 6 and, more particularly, from 1 to 4 carbon atoms; a cyclohexyl radical; or a phenyl radical; and n is an integer of from 2 to 4.

In the context of the present disclosure, however, it is crucial that the polyisocyanates $R^1$ $(NCO)_n$ on which the carbamic acid esters are based should have a boiling point under the decomposition conditions, i.e. under the pressure conditions in the sump of the column (4), which is at least 10° C. below or above the boiling point of the particular alcohol $R^2OH$, and preferably at least 40° C., below or above the boiling point of the particular alcohol $R^2OH$. In general, the polyisocyanates have a higher boiling point than the alcohols so that the polyisocyanates accumulate as fraction I at the lower end of the dephlegmator (5). In the opposite case where the polyisocyanates have a lower boiling point than the alcohols, the alcohol component II would of course accumulate as the lower fraction and the polyisocyanate component I as the upper fraction.

Particularly preferred carbamic acid esters for the process according to the invention are those corresponding to the general formula $$R^1(NHCOOR^2)_2$$

in which $R^1$ is the hydrocarbon radical linking the isocyanate groups of 1,6-diisocyanatohexane, 1-isocyanato-3,3,5-trimethyl-5-isocyanatomethyl cyclohexane, 2,4-diisocyanatotoluene, 2,6-diisocyanatotoluene, 2,2'-, 2,4'-or 4,4'-diisocyanatodiphenyl methane, 2,4'- or 4,4'-diisocyanatodicyclohexyl methane or 1,5-diisocyanatonaphthalene and $R^2$ is a $C_{1-4}$ alkyl radical.

Examples of suitable carbamic acid esters are
1-(butoxycarbonylamino)-3,3,5-trimethyl-5-(butoxycarbonylaminomethyl)-cyclohexane,
1-(methoxycarbonylamino)-3,3,5-trimethyl-5-(methoxycarbonylaminomethyl)-cyclohexane,
1-methyl-2,4-bis-(methoxycarbonylamino)-benzene,
1-methyl-2,6-bis-(methoxycarbonylamino)-benzene,
1-methyl-2,4-bis-(butoxycarbonylamino)-benzene,
1-methyl-2,6-bis-(butoxycarbonylamino)-benzene,
1,10-bis-(methoxycarbonylamino)-decane,
1,12-bis-(butoxycarbonylamino)-dodecane,
1,12-bis-(methoxycarbonylamino)-dodecane,
1,12-bis-(phenoxycarbonylamino)-dodecane,
1,3-bis-(ethoxycarbonylaminomethyl)-benzene,
1,3-bis-(methoxycarbonylamino)-benzene,
1,3-bis-[(methoxycarbonylamino)-methyl]-benzene,
1,3,6-tris-(methoxycarbonylamino)-hexane, 1,3,6-tris-(phenoxycarbonylamino)-hexane,
1,4-bis-(ethoxycarbonylamino)-butane,
1,4-bis-(ethoxycarbonylamino)-cyclohexane,
1,5-bis-(butoxycarbonylamino)-naphthalene,
1,6-bis-(methoxycarbonylamino)-hexane,
1,6-bis-(ethoxycarbonylamino)-hexane,
1,6-bis-(butoxycarbonylamino)-hexane,
1,5-bis-(methoxycarbonylamino)-pentane,
1,6-bis-(methoxymethylcarbonylamino)-hexane,
1,8-bis-(ethoxycarbonylamino)-octane,
1,8-bis-(phenoxycarbonylamino)-4-(phenoxycarbonylaminomethyl)-octane,
2,2'-bis-(4-propoxycarbonylaminophenyl)-propane,
2,4'-bis-(ethoxycarbonylamino)-diphenyl methane,
2,4-bis-(methoxycarbonylamino)-cyclohexane,
4,4'-bis-(ethoxycarbonylamino)-dicyclohexane methane,
2,4'-bis-(ethoxycarbonylamino)-diphenyl methane,
4,4'-bis-(methoxycarbonylamino)-2,2'-dicyclohexyl propane,
4,4'-bis-(methoxycarbonylamino)-biphenyl,
4,4'-bis-(butoxycarbonylamino)-2,2'-dicyclohexyl propane,
4,4'-bis-(phenoxycarbonylamino)-dicyclohexyl methane and
4,4'-bis-(phenoxycarbonylamino)-diphenyl methane.

The "butoxy groups" mentioned are always n-butoxy groups.

Suitable high boilers for carrying out the process according to the invention are liquids or solids of which the boiling points under the pressure conditions prevailing in the sump of a column (4) are at least 10° C., and preferably at least 40° C., above the boiling points of the isocyanates and alcohols on which the carbamic acid esters to be decomposed are based and which, in addition, satisfy the following requirements:

a) they must substantially dissolve both the carbamic acid esters used as starting materials and the isocyanate derivatives formed as secondary reaction products under the decomposition conditions, b) they must show high thermal stability under the decomposition conditions, c) they must be substantially chemically inert to the carbamic acid esters used and to the isocyanates formed, d) they must be substantially distillable under the decomposition conditions, e) they must be substantially removable from the secondary reaction products by distillation, f) they must be substantially recyclable.

In line with these requirements, the hydrocarbons mentioned in U.S. Pat. No. 3,919,278, herein incorporated by reference, are examples of suitable high boilers for the purposes of the invention. Other suitable high boilers are, for example, the various isomeric benzyl toluenes, terphenyls, phthalic acid di(ar)alkyl esters, o-phosphoric acid tri(ar)alkyl esters containing from about 1 to 10 carbon atoms in the (ar)alkyl groups, or mixtures of such compounds. Technical dibenzyl toluene, benzyl n-butyl phthalate, or technical terphenyl are particularly preferred.

In the practical application of the process according to the invention, solutions of from about 5 to 90% by weight, and preferably from about 50 to 80% by weight, of the carbamic acid esters in one of the high boilers mentioned by way of example or a mixture thereof, are used.

These solutions are heated to a temperature of from about 100° to 400° C., and preferably to a temperature of 100° to 300° C., in the heat exchanger (3) under a pressure above the decomposition pressure, and preferably in the range from 3 to 100 bar, and are continuously introduced or expanded as a sidestream into the sump-heated decomposition column. The point at which they are introduced into the column is preferably situated in the lower half thereof, but above the sump.

The decomposition columns suitable for the process according to the invention correspond to conventional distillation columns in various forms and may be very differently designed. The column may be filled with packing elements of various kinds, for example Raschig rings or cloth packs of metal or glass, or may contain separation plates, such as bubble plates. The distillation columns merely have to lend themselves to operation in such a way that the carbamic acid esters introduced into the decomposition column can be uniformly dispersed and the gaseous/liquid products/high boilers can be removed from the distillation column. The sidestream is introduced through a suitable device, for example, in the form of a nozzle or pressure-retaining valve.

The pressure measured in the sump of the column while the process according to the invention is being carried out is in the range from about 0.001 to 5 bar, and preferably in the range from about 10 to 500 mbar. The temperature in the sump of the column is in the range from 150° to 400° C., and preferably in the range from 200° to 300° C. The temperature and pressure conditions are otherwise adjusted within these ranges in such a way that the high boiler used boils in the sump and a continuous depletion of carbamic acid ester occurs in the column upwards from the point at which the sidestream is introduced.

The decomposition products are selectively condensed at the head of the column, the polyisocyanate with the higher boiling point generally being condensed in the dephlegmator (5) and collected as Fraction I in (9) while the alcohol component with the lower boiling point is only condensed in the condenser (6) and is collected as Fraction II in the tank (10). If necessary, the Fractions I and/or II may of course be subjected to working up by distillation. Fraction I, in particular, may be freed from entrained high boiler which is collected as distillation residue and may be reused for the preparation of the starting solution. In general, at least 90% of fractions I and II consist of polyisocyanate $R^1(NCO)_n$ and alcohol $R^2OH$, respectively.

At the same time, the high boiler is continuously removed, for example, through a sump overflow, in a quantity which substantially corresponds to the quantity of high boiler introduced with the carbamic acid solution. In addition, the high boiler removed via the sump outlet, i.e. via the sump overflow, and collected, for example, in the sump drainage tank (8), contains small quantities of low-volatility secondary reaction products so that, in many cases, it is advisable to work up the high boiler removed by distillation before it is reused.

One particular advantage of the process according to the invention is that the polyisocyanates formed during the decomposition reaction are rapidly removed from the reaction zone in gaseous form, are purified by distillation and are only minimally exposed to heat. The result of this is that the secondary reactions of isocyanates known per se are largely suppressed so that a high degree of purity and a high yield of end product (polyisocyanate) of more than 90% are obtained.

In the following Examples, all percentages are by weight.

EXAMPLES

Examples 1 to 9

Description of the apparatus (cf. drawing)

An evacuated double-jacketed column of glass with a diameter of 25 mm and an effective length of 400 mm which is filled with glass Raschig rings (6×6 mm) is used as the decomposition column (4). The solution of the carbamic acid ester is introduced into the lower half of the column via a heated pump (2) and a heat exchanger (3) through a pressure-retaining valve (not shown) which is adjusted to 5 bar. The high boiler and the secondary reaction products are removed by overflow from the column sump. The decomposition products are removed at the head of the column via two removal plates below the dephlegmator (5) and between the dephlegmator and the condenser (6). In all the Examples, the alcohols have a lower boiling point than the diisocyanates formed.

Procedure

The reaction conditions, analytical data and yields of end products are shown in the following Table. To carry out the process, the sump of the column is filled with 100 g of high boiler. The high boiler is then heated to the decomposition temperature under a corresponding vacuum. 600 g of a solution of bisurethane in the high boiler is introduced into the decomposition column over a period of 6 hours. After an operating time of 4 hours, the column is in the equilibrium state. Fraction I is then removed at the lower removal plate while fraction II is removed at the upper removal plate. The yield is based on the diisocyanate present in fraction I. The analyses were carried out by supercritical fluid chromatography (SFC).

Abbreviations

Carbamic Acid Esters

MIPDU: 1-(methoxycarbonylamino)-3,3,5-trimethyl-5-(methoxy carbonylaminomethyl)-cyclohexane
MHDU: 1,6-bis-(methoxycarbonylamino)-hexane
BHDU: 1,6-bis-(n-butoxycarbonylamino)-hexane
MTDU: 1-methyl-2,4-bis-(methoxycarbonylamino)-benzene

High Boilers

DBT: dibenzyl toluene (technical isomer mixture)
BBP: benzyl n-butyl phthalate
TER: technical terphenyl
Monoisocyanate: partly decomposed intermediate product containing urethane and isocyanate groups

| Example No. | | | | 1 | 2 | 3 | 4 | 5 |
|---|---|---|---|---|---|---|---|---|
| Bisurethane | | | | MIPDU | MIPDU | MHDU | MHDU | BHDU |
| High boiler | | | | DBT | BBP | DBT | BBP | DBT |
| Concentration | | | % | 60 | 60 | 60 | 60 | 60 |
| Temperature, sump | | | °C. | 260 | 260 | 260 | 260 | 260 |
| Pressure, sump | | | mbar | 35 | 50 | 35 | 50 | 35 |
| Condenser | | | °C. | −78 | −78 | −78 | −78 | 30 |
| Dephlegmator | | | °C. | 80 | 80 | 80 | 80 | 110 |
| Weighed out | Fraction I | | g/h | 12.1 | 11.4 | 14.4 | 14.6 | 16.7 |
| | Fraction II | | g/h | 47.1 | 47.4 | 42.6 | 43.0 | 42.7 |
| | Sump overflow | | g/h | 40.2 | 41.2 | 40.7 | 41.6 | 40.5 |
| | Fraction II | Alcohol | % | 99.6 | 99.2 | 99.9 | 99.1 | 94.5 |

-continued

| Analysis | Fraction I | Bisurethane | % | 0.4 | 0.6 | 0.1 | 0.9 | 5.5 |
|---|---|---|---|---|---|---|---|---|
| | | Diisocyanate | % | 93.6 | 94.6 | 97.6 | 95.9 | 94.4 |
| | | Monoisocyanate | % | 1.8 | 2.1 | 2.0 | 2.7 | 4.0 |
| | | Bisurethane | % | 0.0 | 0.7 | 0.0 | 0.2 | 1.3 |
| | | High boiler | % | 1.9 | 2.6 | 0.4 | 1.2 | 0.3 |
| | Sump over- flow | Diisocyanate | % | 0.0 | 0.1 | 0.0 | 0.1 | 0.2 |
| | | Monoisocyanate | % | 0.0 | 0.1 | 0.0 | 0.1 | 0.1 |
| | | Bisurethane | % | 0.1 | 0.0 | 0.1 | 0.5 | 0.3 |
| | | High boiler | % | 99.4 | 97.2 | 98.3 | 96.1 | 98.8 |
| | | Secondary products | % | 0.5 | 2.6 | 1.6 | 3.2 | 0.6 |
| Yield theoret. | | | % of | 97.4 | 96.3 | 95.6 | 94.9 | 92.8 |

| | Example No. | | | 6 | 7 | 8 | 9 |
|---|---|---|---|---|---|---|---|
| | Bisurethane | | | BHDU | BHDU | MIDU | MIDU |
| | High boiler | | | BBP | TER | DBT | TER |
| | Concentration | | % | 60 | 60 | 50 | 50 |
| | Temperature, sump | | °C. | 260 | 260 | 240 | 230 |
| | Pressure, sump | | mbar | 50 | 35 | 20 | 25 |
| | Condenser | | °C. | 30 | 30 | −78 | −78 |
| | Dephlegmator | | °C. | 110 | 110 | 80 | 80 |
| Weighed out | Fraction I | | g/h | 15.1 | 14.6 | 12.1 | 10.6 |
| | Fraction II | | g/h | 43.6 | 44.7 | 36.5 | 37.4 |
| | Sump overflow | | g/h | 41.3 | 40.7 | 50.6 | 51.0 |
| Analysis | Fraction II | Alcohol | % | 94.6 | 95.3 | 99.8 | 99.3 |
| | | Bisurethane | % | 5.4 | 4.7 | 0.2 | 0.7 |
| | Fraction I | Diisocyanate | % | 91.8 | 92.1 | 94.0 | 92.2 |
| | | Monoisocyanate | % | 1.5 | 2.3 | 3.6 | 4.3 |
| | | Bisurethane | % | 5.3 | 1.8 | 1.7 | 0.2 |
| | | High boiler | % | 1.4 | 3.8 | 0.7 | 3.3 |
| | Sump over- flow | Diisocyanate | % | 0.2 | 0.1 | 0.2 | 0.3 |
| | | Monoisocyanate | % | 0.0 | 0.2 | 0.0 | 0.1 |
| | | Bisurethane | % | 0.2 | 0.2 | 0.3 | 0.1 |
| | | High boiler | % | 96.9 | 98.2 | 98.9 | 98.0 |
| | | Secondary products | % | 2.7 | 1.3 | 0.6 | 1.5 |
| Yield theoret. | | | % of | 92.1 | 94.7 | 93.8 | 94.3 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the continuous catalyst-free production of polyisocyanates by thermal decomposition, comprising the steps of a) heating a 5 to 90% by weight solution of carbamic acid esters which correspond to the polyisocyanates in a high boiler above the decomposition pressure to a temperature of 100° to 400° C. and above the melting point of the polyurethane, wherein said high boiler
      1) is a solvent for the carbamic acid esters,
      2) is inert to the carbamic acid esters and the decomposition products,
      3) boils under the pressure and temperature conditions prevailing in the sump of the distillation column, and
      4) has a boiling point under those pressure conditions which is at least 10° C. above the boiling point of the polyisocyanate formed, b) subsequently, introducing said solution into a sump-heated distillation column as a sidestream, wherein said distillation column serves as a decomposition reactor, c) maintaining a pressure of 0.001 to 5 bar and a temperature of 150° to 400° C. in the sump to ensure the high boiler continues to boil, d) simultaneously condensing the decomposition products continuously and selectively at the head of the distillation column into two separate fractions, e) subsequently separating said fractions into Fraction I which consists predominantly of the isocyanate component and into Fraction II which consists predominantly of the alcohol component of the carbamic acid ester, and f) continuously removing the high boiler via the sump outlet in a quantity which substantially corresponds to the quantity of high boiler introduced into the column as a solvent for the carbamic acid ester.

2. The process of claim 1, wherein fractions I and II are separately subjected to fine distillation with the distillation residues being returned to the distillation column together with the carbamic acid ester solution to be introduced into the distillation column.

3. The process of claim 1, characterized in that the sump outflow is worked up by distillation and the high boiler accumulating as distillate is reused as solvent for the carbamic acid esters to be split.

4. The process of claim 1, wherein at least one compound corresponding to the formula $$R^1(NHCOOR^2)_2$$

in which

R$^1$ is the hydrocarbon radical linking the isocyanate groups of 1,6-diisocyanatohexane, 1-isocyanato-3,3,5-trimethyl-5-isocyanatomethyl cyclohexane, 2,4-diisocyanatotoluene, 2,6-diisocyanatotoluene, 2,2'-, 2,4'-or 4,4'-diisocyanatodiphenyl methane, 2,4'- or 4,4'-diisocyanatodicyclohexyl methane or 1,5-diisocyanatonaphthalene and
$R^2$ is a $C_{1-4}$ alkyl radical,
is used as the carbamic acidester.

5. The process of claim 1, wherein the bis-O-alkyl urethanes of 1,6-diisocyanatohexane, 1-isocyanato-3,3,5-trimethyl-5-isocyanatomethyl cyclohexane, 2,4-diisocyanatotoluene or mixtures thereof with 2,6-diisocyanatotoluene containing 1 to 4 carbon atoms in the alkyl group are used as the carbamic acid esters.

6. The process of claim 1, characterized in that benzyl toluenes, terphenyls, phthalic acid di(ar)alkyl esters or o-phosphoric acid tri(ar)alkyl esters containing $C_{1-10}$ (ar)alkyl groups are used as the high boilers.

* * * * *